United States Patent
Hansen et al.

(10) Patent No.: US 11,965,823 B2
(45) Date of Patent: Apr. 23, 2024

(54) METHOD OF CORRECTING FOR AN AMPLITUDE CHANGE IN A SPECTROMETER

(71) Applicant: Foss Analytical A/S, Hilleroed (DK)

(72) Inventors: Per Waaben Hansen, Hilleroed (DK); Jeppe Sandvik Clausen, Hilleroed (DK)

(73) Assignee: FOSS Analytical A/S, Hilleroed (DK)

( * ) Notice: Subject to any disclaimer, the term of this patent is extended or adjusted under 35 U.S.C. 154(b) by 277 days.

(21) Appl. No.: 17/629,532

(22) PCT Filed: May 29, 2020

(86) PCT No.: PCT/IB2020/055099
§ 371 (c)(1),
(2) Date: Jan. 24, 2022

(87) PCT Pub. No.: WO2021/038316
PCT Pub. Date: Mar. 4, 2021

(65) Prior Publication Data
US 2022/0252505 A1 Aug. 11, 2022

(30) Foreign Application Priority Data

Aug. 28, 2019 (DK) .............................. PA201901010

(51) Int. Cl.
*G01N 21/27* (2006.01)
*G01N 21/3577* (2014.01)
(Continued)

(52) U.S. Cl.
CPC ....... *G01N 21/274* (2013.01); *G01N 21/3577* (2013.01); *G01N 2021/3595* (2013.01);
(Continued)

(58) Field of Classification Search
CPC .. G01N 2201/129; G01N 21/35; G01N 21/39; G01N 21/3563; G01N 2201/12;
(Continued)

(56) References Cited

U.S. PATENT DOCUMENTS

| 5,870,193 A | * | 2/1999 | Sumiya | ................ G01N 21/274 250/339.08 |
| 6,049,762 A | * | 4/2000 | Ganz | ....................... G01J 3/453 356/325 |

(Continued)

FOREIGN PATENT DOCUMENTS

| EP | 1418417 A2 | 5/2004 | |
| EP | 1464273 A1 | * 10/2004 | ......... A61B 5/14532 |

(Continued)

OTHER PUBLICATIONS

Lidia Esteve Agelet et al: "A Tutorial on Near Infrared Spectroscopy and Its Calibration", Critical Reviews in Analytical Chemistry, vol. 40, No. 4, Nov. 5, 2010, pp. 246-260, XP055508230.
(Continued)

*Primary Examiner* — Michael P Stafira
(74) *Attorney, Agent, or Firm* — Harness, Dickey & Pierce, P.L.C.

(57) ABSTRACT

A method of correcting for an amplitude change in a spectrometric instrument output includes: exposing a sample in a sample holder to electromagnetic radiation at a plurality of wavenumbers; detecting electromagnetic absorption intensities in the sample at the plurality of wavenumbers; providing to a computer device the detected electromagnetic absorption intensities indexed against wavenumber as spectral data; applying in the computer device a mathematical transform (Icorr) to the spectral data to correct for an amplitude change in the spectrometric instrument's output and calculated by determining a difference ($\Delta(SBZ)/$) between first derivatives of a logarithmic transformation of (Continued)

spectral data ($SB_Z$) from the zero material sample at two different wavenumber ranges ($\log_{10}(SB_Z(x_1))'$ and $\log_{10}(SB_Z(x_2))'$); and calculating the mathematical transform (Icorr) as a function inversely dependent on the determined difference ($\Delta(SBZ)/$).

13 Claims, 8 Drawing Sheets

(51) Int. Cl.
  *G01N 21/35* (2014.01)
  *G01N 33/04* (2006.01)
(52) U.S. Cl.
  CPC ..... *G01N 33/04* (2013.01); *G01N 2201/1214* (2013.01); *G01N 2201/129* (2013.01)
(58) Field of Classification Search
  CPC . G01N 2201/06113; G01N 2021/3595; G01N 33/49; G01N 2021/399; G01N 21/359; G01N 21/88; G01N 2201/061; G01N 2201/062; G01N 2201/08; G01N 33/02; G01N 33/15; G01N 33/442; G01N 21/3504; G01N 21/85; G01N 21/9508; G01N 2201/0221; G01N 33/025; G01N 2201/0612; G01N 2021/3513; G01N 2021/1793; G01N 21/658; G01N 21/274; G01N 21/3577; G01N 21/45; G01N 2201/0214; G01N 2201/0216; G01N 2201/0691; G01N 2333/00; G01N 2021/1725; G01N 21/1717; G01N 1/30; G01N 2001/305; G01N 2021/396; G01N 2021/757; G01N 21/171; G01N 33/54373; G01N 21/1702; G01N 21/314; G01N 21/41; G01N 21/636; G01N 21/65; G01N 29/46; G01N 2021/656; G01N 2201/1214; G01N 33/04; G01N 2021/0346; G01N 2021/1704; G01N 21/0303; G01N 21/11; G01N 21/4795; G01N 21/6486; G01N 21/956; G01N 33/536; G01N 2021/1708; G01N 2021/1789; G01N 2021/451; G01N 2021/4709; G01N 2021/653; G01N 21/3151; G01N 21/3581; G01N 21/55; G01N 21/6408; G01N 2201/067; G01N 2201/0697; G01N 2201/1215; G01N 2291/02809; G01N 29/2425; G01N 2021/058; G01N 2021/3133; G01N 2021/3174; G01N 2021/3181; G01N 2021/655; G01N 2021/8848; G01N 21/03; G01N 21/031; G01N 21/05; G01N 21/19; G01N 21/21; G01N 21/3586; G01N 21/4133; G01N 21/47; G01N 21/49; G01N 21/552; G01N 21/8483; G01N 21/8806; G01N 21/94; G01N 2201/0696; G01N 2291/014; G01N 2291/0231; G01N 2291/02433; G01N 2291/02475; G01N 2291/02872; G01N 2291/0421; G01N 2291/044; G01N 2291/101; G01N 2291/102; G01N 29/0609; G01N 29/07; G01N 29/11; G01N 29/12; G01N 29/2418; G01N 29/343; G01N 29/44; G01N 29/48; G01N 33/483; G01N 33/53; G01N 1/38; G01N 2001/383; G01N 2001/388; G01N 2021/1712; G01N 2021/1721; G01N 2021/6421; G01N 2021/6484; G01N 2021/7789; G01N 2021/845; G01N 21/27; G01N 21/33; G01N 21/3554; G01N 21/59; G01N 21/6428; G01N 21/6456; G01N 21/7746; G01N 2201/0627; G01N 2201/0686; G01N 2201/1296; G01N 27/3271; G01N 29/222; G01N 29/30; G01N 33/0016; G01N 33/2841; G01N 33/2847; G01N 33/4833; G01N 33/66
  See application file for complete search history.

(56) References Cited

U.S. PATENT DOCUMENTS

| | | |
|---|---|---|
| 9,874,515 B2 | 1/2018 | Hansen |
| 2005/0037505 A1 | 2/2005 | Samsoondar |
| 2007/0181795 A1 | 8/2007 | Walsh et al. |
| 2012/0035442 A1 | 2/2012 | Barman et al. |

FOREIGN PATENT DOCUMENTS

| | | | | |
|---|---|---|---|---|
| JP | 2012505983 A | * | 3/2012 | |
| KR | 20180048644 A | * | 5/2018 | |
| WO | WO-1992/15008 A1 | | 9/1992 | |
| WO | WO-2013026466 A1 | * | 2/2013 | ............... G01J 3/28 |
| WO | WO-2014194935 A1 | * | 12/2014 | ............ G01J 3/0291 |

OTHER PUBLICATIONS

Asmund Rinnan et al: "Review of the most common pre-processing techniques for near-infrared spectra", TrAC Trends in Analytical Chemistry, vol. 28, No. 10, Nov. 1, 2009, pp. 1201-1222, XP055261058.
Robert P. Cogdill et al: "Process analytical technology case study: Part II. Development and validation of quantitative near-infrared calibrations in support of a process analytical technology application for real-time release", AAPS PharmSciTech, vol. 6, No. 2, Jun. 1, 2005, pp. E273-E283, XP055015472.
Jensen PS et al: "Fourier Transform Infrared Spectroscopy of Aqueous Solutions using Optical Subtraction", Proceedings of SPIE/ IS & T, vol. 4624, Jan. 1, 2002, pp. 150-159, XP002399043.
Danish Patent and Trademark Office Search Report For Danish Patent Application No. PA 2019 01010 dated Oct. 18, 2019.
International Search Report for International Application No. PCT/IB2020/055099 dated Aug. 7, 2020.
Written Opinion for International Application No. PCT/IB2020/055099 dated Aug. 7, 2020.

* cited by examiner

METHOD OF CORRECTING FOR AN AMPLITUDE CHANGE IN A SPECTROMETER

CROSS-REFERENCE TO RELATED APPLICATIONS

This application is a National Stage of PCT/IB2020/055099, filed on May 29, 2020, which claims priority to Danish Patent Application PA201901010, filed on Aug. 28, 2019 in the Danish Patent and Trademark Office, the entire contents of each of which are incorporated herein in their entirety.

BACKGROUND

The present invention relates to a method of compensating for an amplitude change in the output of a spectrometer of the type for generating spectral data from unknown samples held in sample holders and in particular to the compensation for amplitude change due to changes in an optical path length through the sample holder.

In typical spectrometers for generating spectral data from unknown samples, a light emitter and a light detector are configured to define a light-path into which the sample in question is positioned in order to have the sample interact with the light. Typically a sample holder, such as comprising a sample cuvette for liquid or particulate samples, is used for holding samples within the light-path in a repeatable manner. The sample holder has an internal sample receiving volume and is provided with surfaces, usually opposing surfaces, at least portions of which are transparent to the light being interacted with the sample. The separation between these transparent portions delimits the optical pathlength through the sample holder and thus through a sample which is being held in the sample holder.

The usual manner of obtaining the necessary spectral data in any spectrometer is by generating a transmittance (or absorbance) spectrum of the sample. To do this a so-called single beam spectrum ($SB_S$) is obtained which comprises spectral data relating to both the sample and the spectrometer. In order to isolate the spectral data related to the sample, a similar single beam spectrum ($SB_Z$) is typically measured on a so-called zero-material, such as water or a water based material if, for example, the sample to be measured is a liquid or air if, for example, the sample to be measured is a solid. Such single beam spectra $SB_Z$ include the same effects which are related to the spectrometer as do the sample spectra $SB_S$ but effects due to the sample are not present. The zero-material spectrum is then employed to provide a wavelength dependent zero level across the spectral region within which the spectral data is collected.

The single beam spectrum of the sample ($SB_S$) is subsequently divided by the single beam spectrum of the zero-material ($SB_Z$) at the same wavelengths throughout the respective spectra in order to obtain a so-called dual beam spectrum of the sample ($DB_S$) which is essentially the transmittance spectrum of the sample relative to the zero-material and relates virtually only to the transmission properties of the sample. As is well known, taking the negative $\log_{10}$ of this provides the absorbance spectrum for the sample. These operations are performed in an arithmetic unit of a computing device which is associated with the spectrometer and which is provided either integral with or separate but in operable connection to the spectrometer, for example in the form of a suitably programmed personal computer.

Over time the output of the spectrometer tends to vary. An aspect of this variation may be described as an amplitude change as a result of which different amplitudes are measured at the same wavelengths for the same sample in two otherwise similar spectrometers or at two runs of the same spectrometer at different times. This is typically caused by the wear of the sample holder causing a change in the separation between the opposing transparent portions and hence to a change in the optical pathlength through the sample holder. As is known, according to the Beer-Lambert law, the absorbance of light by a sample at a given wavenumber (wavelength) is proportional to the optical pathlength through the sample. Thus as the sample holder wears and the optical pathlength changes then the amplitude of the output of the spectrometer changes and needs to be compensated for at regular intervals.

In order to compensate for an amplitude change of the spectrometer, it is usual that the spectrometer is periodically standardised. Such a standardisation is known from U.S. Pat. No. 9,874,515 which discloses a method of determining a pathlength deviation through a sample in a cuvette. The method comprises: exposing the sample to electromagnetic radiation at a plurality of wavenumbers, determining electromagnetic absorption in the sample at the plurality of wavenumbers, determining a first wavenumber associated with a first absorption level of an absorption band, particularly a water absorption band in the zero beam absorption spectrum ($SB_Z$) of the zero liquid, and a second wavenumber associated with a second absorption level of that absorption band, wherein the second wavenumber is different from the first wavenumber, determining a difference between the first wavenumber and the second wavenumber, and determining the pathlength deviation based on the difference. From this pathlength difference an intensity variation may be calculated using the Beer-Lambert law and compensated for in subsequent spectral measurements.

Unfortunately the so recorded zero beam absorption spectrum ($SB_Z$) includes information not only on the zero material (for example the zero liquid) in the cuvette but also background information on elements, including those in atmospheric air, within the light-path between the light emitter and the light detector which is unrelated to the zero material but which influences the light intensity.

As is disclosed in U.S. Pat. No. 9,874,515, this background information may be determined using an air measurement, i.e. a measurement in which the cuvette only comprises air. In this case, the sample is absent during the spectral analysis, and a single-beam spectrum comprises information only about the sample cuvette, the air within the cuvette, reflection of mirrors, emission spectrum of the electromagnetic source, the sensitivity of the detector, etc. However, the separation between the opposing transparent windows of the typical cuvette is around 50 µm which makes it difficult to ensure that all sample is removed and only air is present in the cuvette during such background measurements. Dismantling and thoroughly drying the cuvette for each compensation measurement is impractical, as is replacing the sample cuvette with a dry one for each compensation measurement.

In order to avoid this it is also known from U.S. Pat. No. 9,874,515 to make a mathematical estimation of the background spectrum. Such estimation has shown to be insufficiently accurate in certain circumstances and for certain applications.

SUMMARY

According to a first aspect of the invention there is provided a method of correcting for an amplitude change in an output of a spectrometric instrument, the method comprises exposing an unknown sample in a sample holder to electromagnetic radiation at a plurality of wavenumbers; detecting by the spectrometric instrument electromagnetic absorption intensities in the unknown sample at the plurality of wavenumbers; making accessible to a computer device associated with the spectrometric instrument the detected absorption intensities indexed against wavenumber as spectral data; and applying by means of the computer device a mathematical transform to the spectral data to correct for an amplitude change in the output of the spectrometric instrument; wherein the method further comprises calculating in the computer device the mathematical transform by determining a difference between absorbance values at two different wavenumber ranges in a first derivative of spectral data, being detected absorption intensities indexed against wavenumber, from a zero material sample; and calculating the mathematical transform as a function inversely dependent on the determined difference. Thus, by calculating the first derivative and subsequently subtracting two signals close to one another dependency on the background spectrum is substantially reduced.

In some embodiments calculating the mathematical transform also comprises calculating a humidity correction factor as slope/intercept on selected humidity regions in the absorption spectrum.

This humidity correction factor effectively compensates for the effects of humidity in background information and has an advantage that this compensation may be made independent of any actual knowledge of the background information.

In these embodiments calculating the mathematical transform comprises determining a difference between absorbance values at two different wavenumber ranges in a first derivative of the spectral data from the zero material sample; and calculating the mathematical transform as a function inversely dependent on the sum of the determined difference and the humidity correction factor.

Usefully the zero material sample is water based, particularly nominally pure water (water in which any impurities or additives make no measurable difference to the measured spectral data of water). This has an advantage that human errors in preparing the zero material sample may be minimized.

BRIEF DESCRIPTION OF THE DRAWINGS

These and other advantages associated with the present invention will become apparent from a consideration of the following description of aspects of non-limiting exemplary embodiments of the present invention which is made with reference to the accompanying figures, of which.

DETAILED DESCRIPTION

Figure 1:
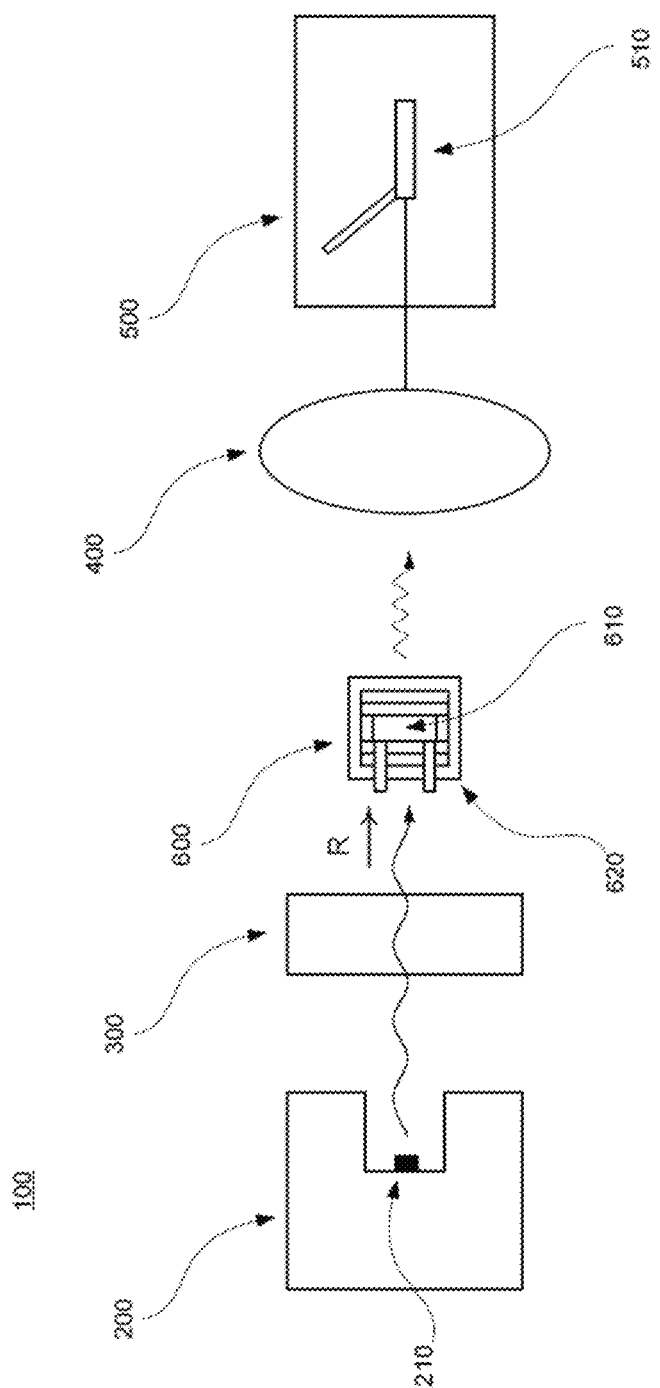
FIG. 1 Illustrates schematically an embodiment of an inventive apparatus according to the present invention.

In the following, an embodiment of the inventive apparatus 100 will be described with reference to FIGS. 1 and 2 in the context of absorption spectroscopy. The apparatus 100 comprises a radiation device 200, an interferometric arrangement 300, a detector 400 and a measuring device 500. Also, a sample holder 600 for holding a sample to be analysed is arranged to be placed in the apparatus 100.

Figure 2:
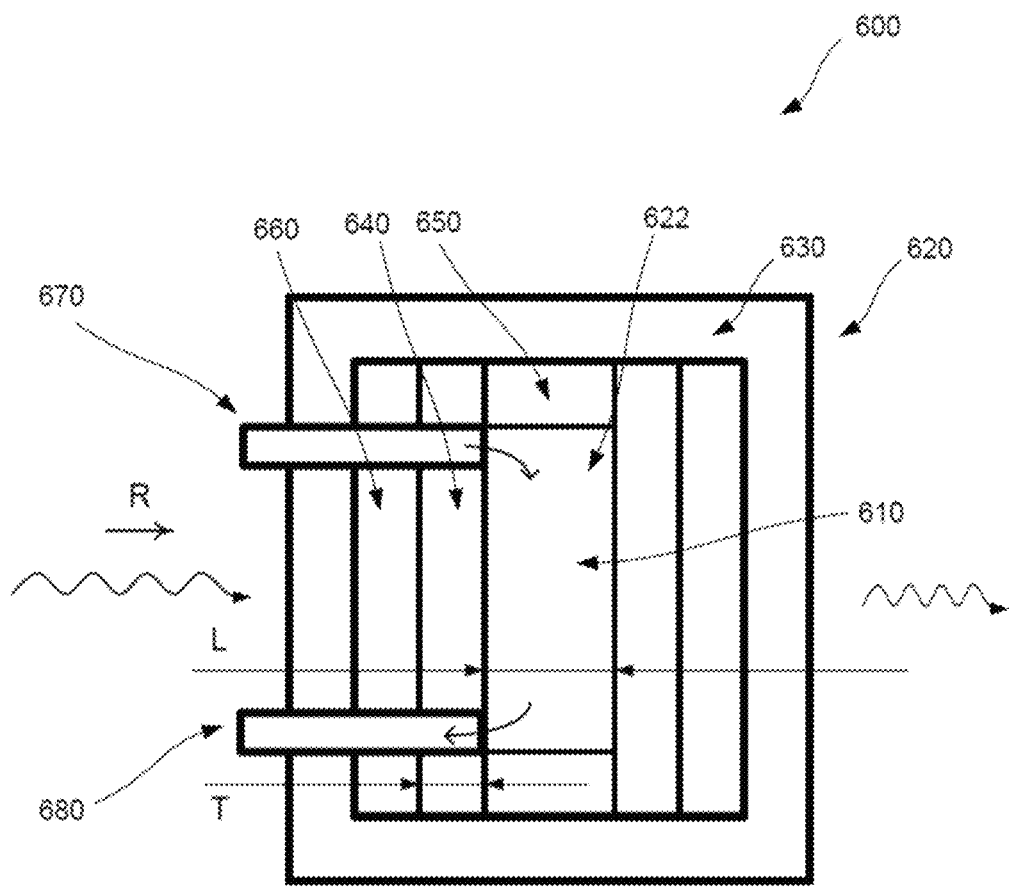
FIG. 2 Illustrates a schematic cross-sectional top view of the sample holder illustrated in FIG. 1.

The radiation device 200 comprises a radiation source 210 which is arranged to emit polychromatic infrared radiation in the direction as indicated by the letter R in FIGS. 1 and 2.

The interferometric arrangement 300 comprises necessary equipment for implementing Fourier transform spectroscopy, as is well-known to a person skilled in the art. For example, the interferometric arrangement 300 comprises a collimator which collimates the infrared radiation and additional equipment comprised in an interferometer, for example optical components such as mirrors and lenses.

The detector 400 is arranged to detect incoming infrared radiation which is transmitted through the sample holder 600, see further below.

The measuring device 500 comprises a computer 510 which is connected to the detector 400 for collecting unprocessed data about the detected infrared radiation. By means of this connection, the measuring device 500 is arranged to determine a transmittance in a discrete number of channels positioned equidistantly along a wavenumber axis. The computer 510 comprises a processor for processing the collected data, suitable computing software, as well as additional equipment well-known to a person skilled in the art. Moreover, the computer 510 is arranged to store the collected data and the processed data in a memory. According to the present embodiment, a routine using Fourier transform algorithms is used in order to transform the unprocessed data from the detector 400 into data about the intensity as a function of the wavenumber. Moreover, the computer 510 is arranged to present the data graphically in terms of two-dimensional plots, see FIGS. 4-8 referred to below.

The radiation device 200, the interferometric arrangement 300, the detector 400 and the measuring device 500 will in the following be referred to as an FTIR spectrometer, or simply a spectrometer. Further below, a method for correcting intensity deviations (or amplitude changes) of this FTIR spectrometer will be described.

The sample holder 600 is placed between the interferometric arrangement 300 and the detector 400. Furthermore, the sample holder 600 is arranged to hold a liquid sample which is to be spectrally analysed by letting infrared radiation be transmitted through it. For instance, the liquid sample may be milk or wine. In the present embodiment, the liquid sample predominantly comprises water 610 which serves as a reference or so-called "zero" fluid and is used in order to perform corrections of cuvette pathlength deviations, see further below. The water sample 610 is placed in a cuvette 620 which is in part made out of calcium fluoride. The outer surface of the cuvette 620 is shaped as a rectangular parallelepiped. The cuvette 620 comprises inner walls 630, window elements 640, spacers 650, cavities 660 and a sample space 622 for holding the sample 610, see the cross-sectional top view in FIG. 2. It is clear that the inner walls 630 and the window elements 640 are transparent to the infrared radiation which is sent through the sample 610. It is noted that the spacers 650 do not need to be transparent. For example, the spacers 650 may be comprised out of a plastic. The volume of the sample space 622 may be varied by varying the extension of the spacers 650. Indeed, the spacers 650 create a pathlength of the cuvette 620. Furthermore, there is an inlet 670 for introducing the sample 610 into the sample space 622 and an outlet 680 for removing the sample 610 from the sample space 622. According some embodiments, the sample 610 is kept in motion during the measurement, flowing from the inlet 670 to the outlet 680 via the sample space 622, as indicated by the arrows in FIG. 2. In other embodiments, however, the sample 610 is kept stationary in the sample space 622 during the measurement, in which embodiments the inlet 670 and the outlet 680 may be omitted.

The distance covered by the infrared radiation in the sample space 622 is referred to as a pathlength. Since the radiation is transmitted through the sample 610 at right angles with respect to a side edge of the cuvette 620, in the direction R in FIG. 1 and FIG. 2, the pathlength L coincides with an inner length extension of the cuvette 620, between the window elements 640. If the cuvette 620 wears down, the pathlength L will change (increase).

In fact, since the window elements 640 making contact with the water sample 610 are made from calcium fluoride, they will be dissolved over time. During its lifetime, the cuvette 620 may also have been deteriorated by other chemicals. For example, the thickness T (see FIG. 2) of the window elements 640 will become smaller over time. Consequently, the pathlength L will increase over time, giving rise to pathlength deviations. In addition, it is noted that cuvettes placed in different apparatuses of the same type 100 by default have different pathlengths. For instance, differing pathlengths may have resulted from having dissolved the cuvettes to various degrees, even if the cuvettes have been substantially similar at some point in time. Moreover, the extension of the spacers 650 may vary between different cuvettes 620, thereby giving rise to varying pathlengths. Therefore, in order to make the characteristics of different apparatuses of the same type 100 more similar and the characteristics of a same apparatus 100 more stable over time, the variation in/of pathlengths need to be compensated for.

Figure 3:
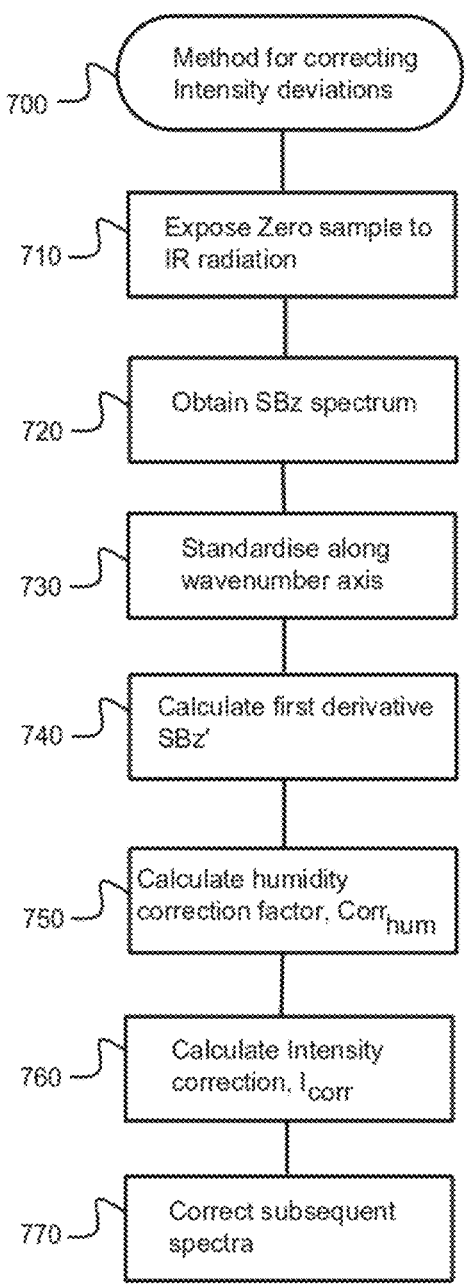
FIG. 3 is a block diagram illustrating a method of determining a correction factor according to an embodiment of the present invention.

An exemplary embodiment of the method of correcting for intensity deviations in the apparatus 100 (here for example an FTIR spectrometer) according to the present invention is described below with reference to the block diagram of FIG. 3. As will be understood further below, a correction of a pathlength deviation also means a correction of an intensity deviation. According to the present exemplary embodiment the method utilizes the single beam spectrum $SB_Z$ of the zero liquid sample, which is here a nominally pure water sample (the water sample may contain small amounts of other components such as around 0.01% by volume detergent), for detecting deviations in cuvette pathlengths. After the spectrometer 100 has been corrected using measurements on the water sample, it may be used for measurements on other liquid samples, such as milk or wine in order to make quantitative determinations of components of interest in these samples in a manner well known in the art.

According to the present method an intensity correction, $I_{corr}$, may be determined which corrects the absorbance values ($A_{samp,L}^w$) of a sample relative to the zero material (here water) measured in a sample holder of a pathlength L to those values ($A_{samp,L0}^w$) measured in a sample holder of standard pathlength $L_0$. This may be described by:

$$A_{samp,L0}^w = I_{corr} \cdot A_{samp,L}^w \quad (1)$$

From this it follows that the intensity correction is a ratio between the two pathlengths as:

$$I_{corr} = L_0/L \quad (2)$$

An aim of the present invention is to provide a method by which $I_{corr}$ may be determined without the use of a reference material having a known absorbance.

A logarithmic transformation of the single beam spectrum of the zero material $SB_Z$, here water, converts the intensity values (y axis values) into absorbance units and the single beam spectrum $SB_Z$ may then be decomposed into its different components, as:

$$\log_{10}(SB_Z) = \log_{10}(SB_{air}) - A_{w,L}^{air} \quad (3)$$

where $SB_{air}$ is the single beam spectrum of air and $A_{w,L}^{air}$ is the absorbance of water relative to air at the pathlength L. From equation (3) it follows that:

$$\log_{10}(SB_Z) = \log_{10}(SB_{air}) - (L/L_0) \cdot A_{w,L0}^{air} \quad (4)$$

where $A_{w,L0}^{air}$ is the absorbance of water relative to air at the pathlength $L_0$. From equation (2) the equation (4) may be re-written as:

$$\log_{10}(SB_Z) = \log_{10}(SB_{air}) - (1/I_{corr}) \cdot A_{w,L0}^{air} \quad (5)$$

In order to reduce the effects of the background, typically to a negligible level, according to the present method a first derivative is calculated. The derivative of the background $SB_{air}$ varies slowly whilst the derivative of the water absorption $SB_Z$ will vary much more quickly, particularly at the rising and the trailing edges of the water absorption bands in the in the single beam spectrum of water $SB_Z$, thus from equation (5):

$$\log_{10}(SB_Z)' = \log_{10}(SB_{air})' - ((1/I_{corr}) \cdot A_{w,L0}^{air})' \quad (6)$$

By obtaining the derivatives at two different wavenumbers (or ranges), $x_1$ and $x_2$ lying close to one another on the x axis (wavenumber axis) it is possible to also neglect any slope in the background. It is preferable that the two different wavenumbers (or ranges), $x_1$ and $x_2$ are selected such that the slopes in the water spectrum relative to air at these points (or ranges) are very different. This may be expressed mathematically as:

$$\log_{10}(SB_Z(x_1))' - \log_{10}(SB_Z(x_2))' = \log_{10}(SB_{air}(x_1))' - \log_{10}(SB_{air}(x_2))' - (1/I_{corr}) \cdot (A_{w,L0}^{air\prime}(x_1) - A_{w,L0}^{air\prime}(x_2)) \quad (7)$$

Which may be more simply re-written as:

$$\Delta(SB_Z)' = \Delta(SB_{air})' - (1/I_{corr}) \cdot \Delta A_{L0}' \quad (8)$$

where:

$$\Delta(SB_Z)' = \log_{10}(SB_Z(x_1))' - \log_{10}(SB_Z(x_2))'$$

is the difference in slope in the measured single beam zero spectrum of water $$\Delta(SB_{air})' = \log_{10}(SB_{air}(x_1))' - \log_{10}(SB_{air}(x_2))'$$

is the difference in slope in the background of the measured single beam zero spectrum of water $$\Delta A_{L0}' = (A_{w,L0}^{air\prime}(x_1) - A_{w,L0}^{air\prime}(x_2))$$

Is the difference in slope of the absorption spectrum of water relative to air at the nominal pathlength Next, the background may be decomposed into a component due to dry air in the light path, $SB_{air,dry}$, and optionally a component due to humidity in the air in the light path $SB_{hum}$, thus:

$$\Delta(SB_{air})' = \Delta(SB_{air,dry})' + \Delta(SB_{hum})' \quad (9)$$

From equation (8) this gives:

$$\Delta(SB_Z)' = \Delta(SB_{air,dry})' + \Delta(SB_{hum})' - (1/I_{corr}) \cdot \Delta A_{L0}' \quad (10)$$

The intensity correct $I_{corr}$ may then be expressed as:

$$(1/I_{corr}) = (\Delta(SB_Z)'/\Delta A_{L0}') + (\Delta(SB_{air,dry})'/\Delta A_{L0}') + (\Delta(SB_{hum})'/\Delta A_{L0}') \quad (11)$$

or:

$$(1/I_{corr}) = c_1 \cdot \Delta(SB_Z)' + c_2 + corr_{hum} \quad (12)$$

The values $c_1$, $c_2$ and a formula for the humidity correction ($corr_{hum}$), when used, needs to be determined experimentally:

- the constant $c_1$ is dependent solely on the absorption of water relative to air at the nominal pathlength $L_0$;
- the constant $c_2$ is the contribution to the background due to dry air, particularly but not essentially this may be a mean contribution over a population of apparatus 100; and
- the correction, $corr_{hum}$, is a correction based on the amplitude of the humidity signature in the single beam spectrum, $SB_Z$, of the zero material (here water) and in some cases where its effects are negligible, may be ignored.

According to the present invention $corr_{hum}$ is calculated as a slope/intercept on selected humidity regions, as:

$$corr_{hum} = -\log_{10}\left[\frac{Peak_1}{Peak_2}\right] c_3 + c_4 \quad (13)$$

- the constant $c_3$ describes the influence of humidity on the intensity correction $I_{corr}$; and
- the constant $c_4$ is the offset between the intensity at the two peak positions when no humidity is present. This approaches zero as $Peak_1$ and $Peak_2$ approach one another.

The humidity (from water in the gas phase, i.e. water vapour) produces an infrared spectrum with a fringe pattern. The ratio between a valley ($Peak_2$) and an adjacent peak ($Peak_1$) in this fringe pattern can be used as a measure for the amount of water vapour in the light path. The constants $c_1$, $c_2$, $c_3$ and $c_4$ are determined empirically by measuring the single beam zero spectrum $SB_z$ of water on one or more apparatus 100 of the same type using cuvettes with pathlengths covering an expected variation, such as 50 μm to 60 μm or from 37 μm to 44 μm. The effect on the spectrum of a known sample (e.g. milk or wine or glycerol or other chemical solution) is collected and the constants are adjusted until all spectra are identical. This task need only be performed once for a given apparatus type and used in the future for all apparatus of this type.)

In some embodiments the x axis (or wavenumber scale) of the single beam spectrum is standardized before the y axis (amplitude) correction is performed. This may be achieved in a manner that is well known in the art by applying a mathematical transform to the spectrum by which transform measured data is standardized along the x axis. In the present exemplary embodiment, the x axis standardization is based on the $CO_2$ peak in the infrared range.

As is known, this x axis standardisation comprises standardising the wavenumber scale of an optical spectrum recorded by the apparatus 100 by providing an optical spectrum recorded by the apparatus 100 and comprising spectral patterns originating from constituents of atmospheric air in the light path in the apparatus 100; selecting a spectral pattern originating from constituents of atmospheric air in the apparatus 100, here $CO_2$ in air; determining one or more wavenumber dependent position values associated with the selected spectral pattern; constructing a mathematical transform based on a difference between the determined value or values and a corresponding reference value or values of the selected spectral pattern and applying the mathematical transform to optical spectra subsequently recorded by the apparatus 100 to standardise the wavenumber scale.

Additionally the humidity correction $corr_{hum}$ may be employed in other methods of determining an intensity correction, such as for example the method disclosed in U.S. Pat. No. 9,874,515, to compensate for background effects.

The exemplary embodiment of the method according to the present invention will now be further described with reference to the block diagram illustrated in FIG. 3. The method (Box 700) comprises an exposure of the zero liquid having a known amount of at least one component (here water sample) 610 to polychromatic infrared radiation (Box 710) from the radiation device 200. The radiation is illustrated by wavy lines in FIG. 1 and FIG. 2. The detector 400 detects the incoming infrared radiation which has been transmitted through the interferometric arrangement 300, the water sample 610 as well as the cuvette 620, thereby determining (Box 720) the intensity levels for wavenumbers in the range between around 900 cm$^{-1}$ and around 3500 cm$^{-1}$, utilizing the measuring device 500. More specifically, the intensity levels for a discrete set of, typically equidistantly distributed, wavenumbers in this range are determined. The intensity data indexed against wavenumber data are stored in the memory of the computer 510 as the single beam spectrum of the zero material, $SB_Z$. The computer 510 processes the stored data using a suitable mathematical transform to obtain (Box 730) $\log_{10}$-transformed intensity (or Absorbance) levels standardised along the x axis (the wavenumber scale).

The first derivative, $\log_{10}(SB_Z)'$, of this absorbance spectrum is calculated (Box 740), at least in the region of the spectrum characterised by water absorption at around 1650 cm$^{-1}$. This may be achieved in the computer 510 using the known Savitzky-Golay algorithm. A difference between two ranges in the first derivative, $\Delta(SB_Z)'$, is calculated (Box 740) where the two ranges are characterised by being close to the water band absorption at around 1650 cm$^{-1}$, preferably on the higher wavenumber shoulder of the water band. In the present embodiment the ranges 1740-1746 cm$^{-1}$ and 1844-1850 cm$^{-1}$ are used. This is illustrated by the broken line constructions in FIG. 4 by which is illustrated a representative first derivative single beam spectra of water obtained by a plurality of instruments 100 of the same type (here four: labelled as Instrument 1, Instrument 2, Instrument 3 and Instrument 4 in the FIG. 4).

The humidity correction, $corr_{hum}$, when used, is calculated (Box 750) according to equation (13) to compensate for the effect of environmental humidity on the intensity correction $I_{corr}$. In the present embodiment the ranges 1832-1840 cm$^{-1}$ ($Peak_1$) and 1814-1822 cm$^{-1}$ ($Peak_2$) are used. This is illustrated by the broken line constructions in FIG. 5 by which is illustrated representative single beam spectra of water obtained by the same plurality (here four) of instruments 100 referenced above with respect to FIG. 4.

The intensity correction, $I_{corr}$, is then calculated (Box 760) as the reciprocal of the inverse intensity correction, $1/I_{corr}$, calculated according to equation (12). This intensity correction, $I_{corr}$, may then be applied (Box 770) to optical spectra subsequently recorded by the apparatus 100 to standardise the absorbance intensity scale (y axis).

Figure 4:
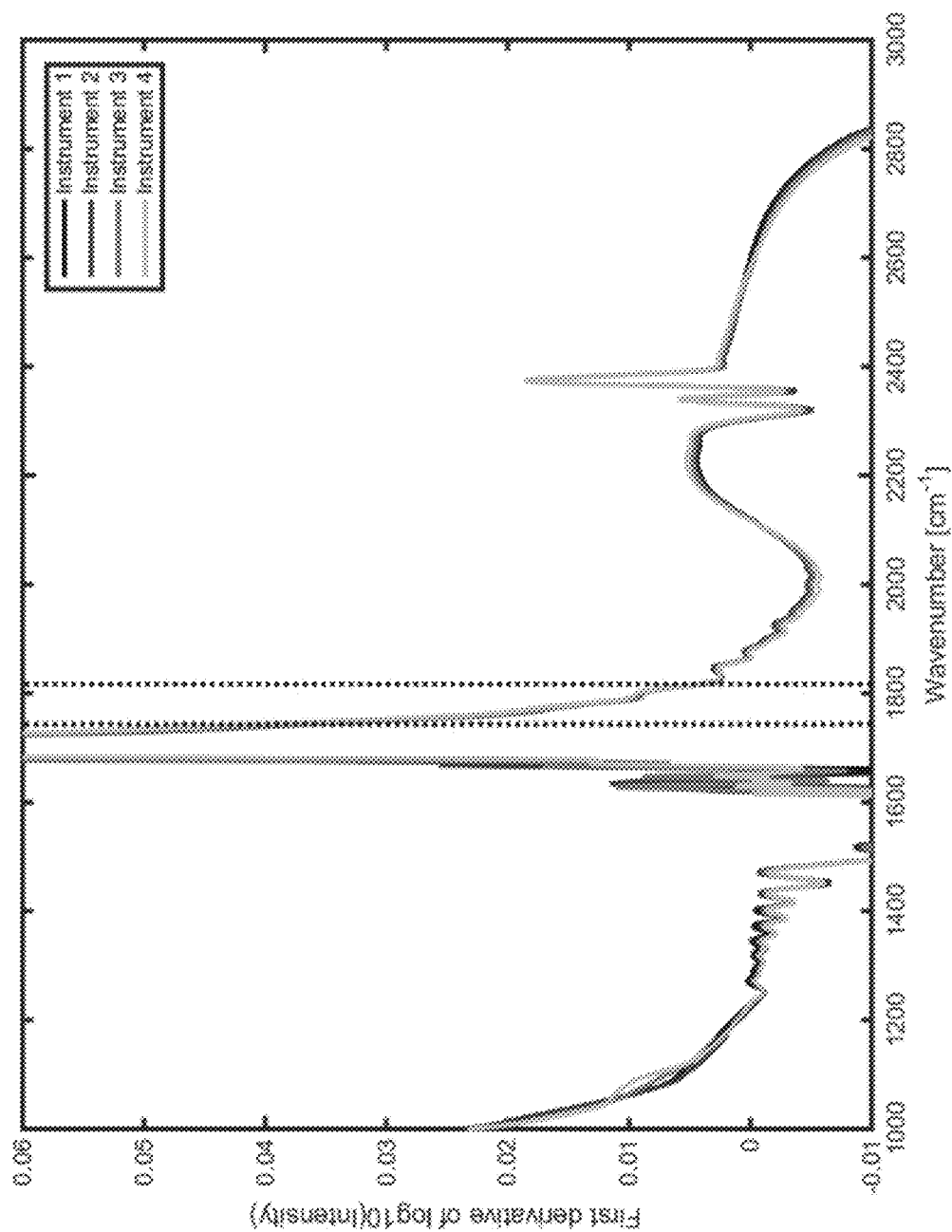
FIG. 4 is a graphical representation of first derivative single beam spectra of water.
Figure 5:
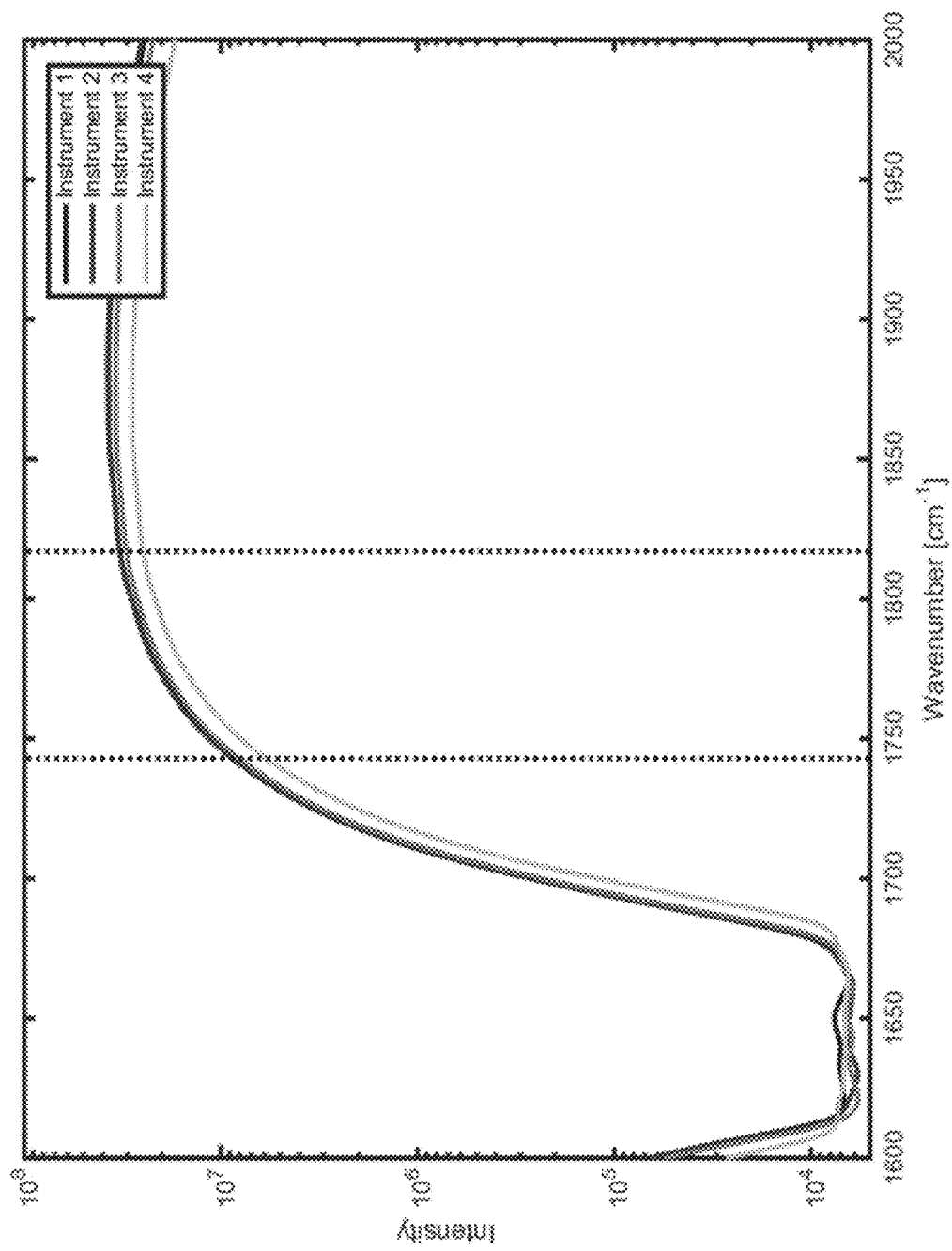
FIG. 5 is a graphical representation of a region of the single beam spectra of water illustrated in FIG. 7 showing wavenumber positions for humidity correction.

An example of the application of this method will now be described in relation to the standardization of the output of a plurality of instruments 100 of the same type, here the four instruments referenced above with respect to FIG. 4 and FIG. 5, measuring on a same milk sample. It will be appreciated that in the following figures which are stated as illustrating measurements made by each of these four instruments the variations between instruments may be so small as to be visually represented as overlapping. Differences between these four instruments may then be better discerned from the numerical values presented in the accompanying tables, Table 1 to Table 3 inclusively.

Figure 6:
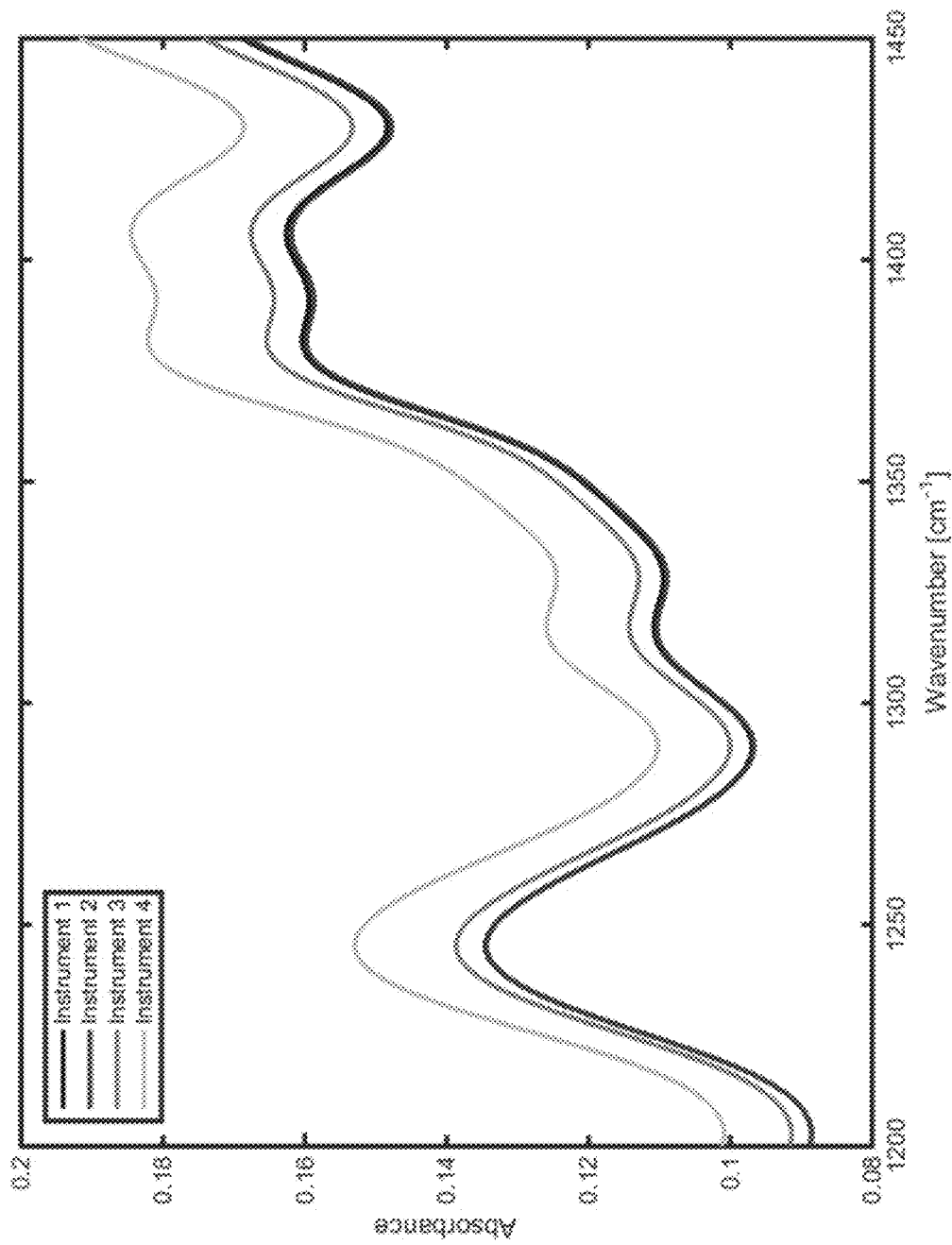
FIG. 6 is a graphical representation of uncorrected absorbance spectra of milk.
Figure 7:
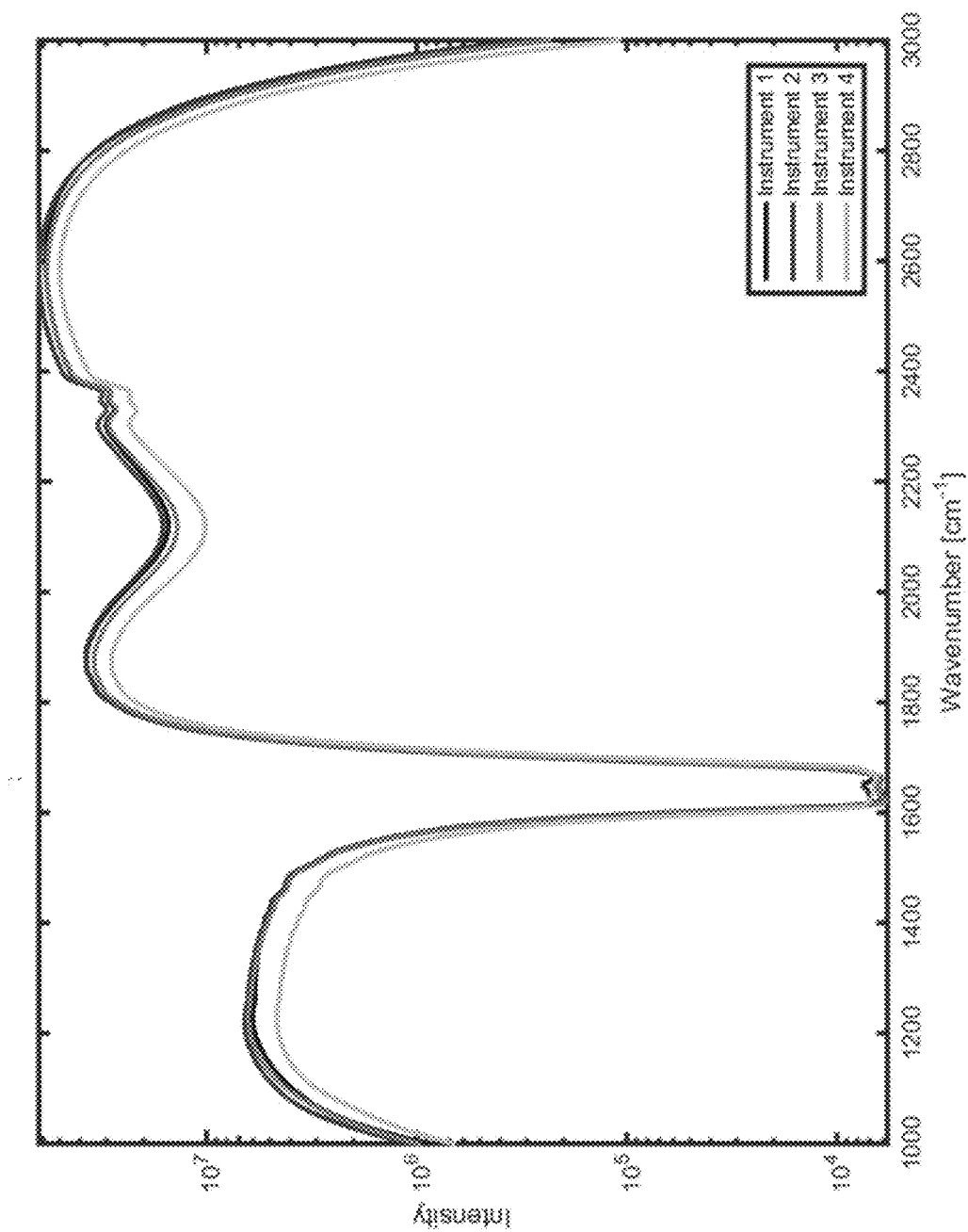
FIG. 7 is a graphical representation of single beam spectra of water.

The resulting absorbance of milk measured on the four different instruments 100 of the same type are plotted in FIG. 6 versus the wavenumbers. Each of the spectra in FIG. 6, is manifested as an interpolating curve in a two-dimensional plot, with magnitude of absorbance on the vertical axis and a corresponding wavenumber on the horizontal spectral axis. According to an alternatively graphical presentation, the plot may be a scatter plot. As can be seen the absorbance values at the same wavenumber differ slightly between instruments. This will lead to differences in the amount of components of the same milk sample being determined chemometrically, from these absorbance spectra in a known manner, in each of the instruments. When applying prediction models for fat, protein, lactose, total solids (TS) and solids non-fat (SNF) to uncorrected spectra of a set of, here fifteen, standard milk samples the following Root Mean Square Errors (RMSEPs) between the instruments and their common mean, are obtained—results in g/100 mL:

TABLE 1

Predicted milk components using corrected spectra for each instrument

|  | Fat | Protein | Lactose | TS | SNF |
| --- | --- | --- | --- | --- | --- |
| Instrument 1 | 0.147 | 0.132 | 0.188 | 0.479 | 0.349 |
| Instrument 2 | 0.134 | 0.141 | 0.195 | 0.490 | 0.352 |
| Instrument 3 | 0.040 | 0.041 | 0.068 | 0.146 | 0.117 |
| Instrument 4 | 0.320 | 0.313 | 0.450 | 1.115 | 0.818 |
| Mean | 0.190 | 0.185 | 0.265 | 0.659 | 0.482 |
| Relative error* | 5.30% | 5.08% | 5.28% | 5.11% | 5.15% |

*The mean error relative to the average concentration of the parameter.

This level of performance is not acceptable to a user requiring virtually identical results from different instruments.

Following the method according to the present invention a single beam spectrum of water ($SB_Z$) is obtained on each of the four instruments (see FIG. 7) and a first derivative of the absorbance spectrum, for each of these single beam spectra, standardised in the wavenumber axis, is determined in the computer 510. These first derivatives are illustrated in FIG. 4, in which the two regions at which the difference $\Delta(SB_Z)'$ is to be calculated are also depicted (broken lines). It can be seen from FIG. 7 and FIG. 4 that the y axis values at each wavenumber are slightly different for each of the four instruments 100. The recorded single beam spectrum is processed by the computer 510 of the instrument 100 which generates the respective spectrum in order to determine the humidity correction, $corr_{hum}$, for each instrument from the intensity values at the two regions illustrated by the broken lines in FIG. 5. In each instrument the associated computer 510 then calculates the intensity correction factor $I_{corr}$, specific to each instrument of the four.

TABLE 2

Intensity correction factors for each instrument

| Instrument | Intensity correction ($I_{corr}$) |
| --- | --- |
| 1 | 0.9979 |
| 2 | 0.9953 |
| 3 | 0.9740 |
| 4 | 0.8823 |

Figure 8:
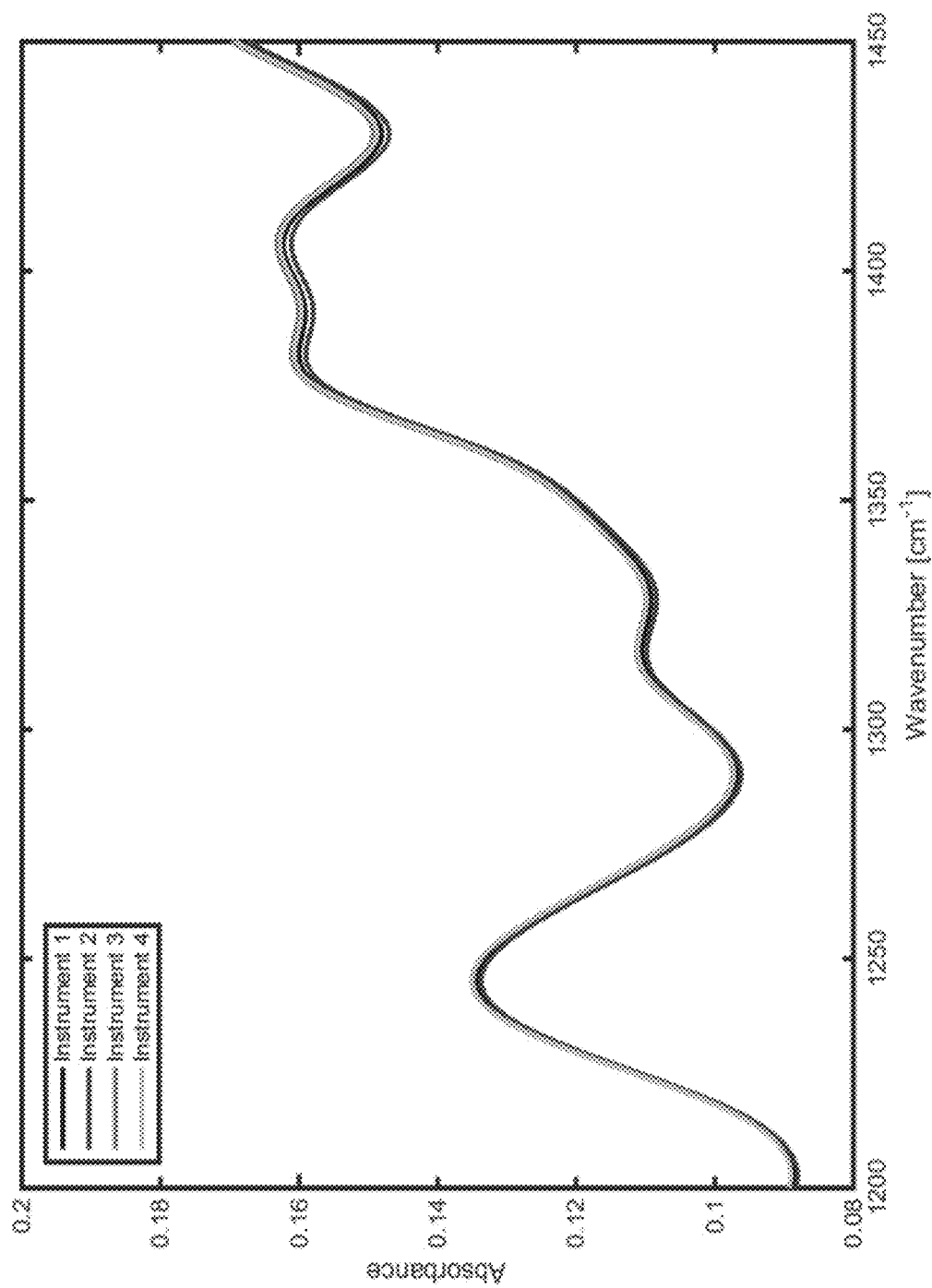
FIG. 8 is a graphical representation of absorbance spectra of milk corrected according to the method of the present invention.

The correction factor $I_{corr}$ for each instrument can then be applied to the absorbance data collected by each instrument (for example the absorbance data for the same milk sample illustrated in FIG. 6) and the corrected (or y axis standardised) absorbance data for each instrument is brought to closer conformity. This is illustrated in FIG. 8 which shows the absorbance spectra of milk that are illustrated in FIG. 6 but each corrected with the appropriate intensity correction factor, $I_{corr}$, for the instrument which records the associated milk spectrum (see Table 2).

When applying this correction to a set of, here fifteen, standard milk samples the following Root Mean Square Errors (RMSEPs) between the instruments and their common mean, are found when predicting fat, protein, lactose, total solids (TS) and solids non-fat (SNF)—results in g/100 mL:

TABLE 3

Predicted milk components using corrected spectra for each instrument

|  | Fat | Protein | Lactose | TS | SNF |
| --- | --- | --- | --- | --- | --- |
| Instrument 1 | 0.007 | 0.011 | 0.006 | 0.013 | 0.010 |
| Instrument 2 | 0.007 | 0.010 | 0.017 | 0.034 | 0.022 |
| Instrument 3 | 0.016 | 0.014 | 0.008 | 0.041 | 0.021 |
| Instrument 4 | 0.012 | 0.017 | 0.010 | 0.022 | 0.012 |
| Mean | 0.011 | 0.014 | 0.011 | 0.030 | 0.017 |
| Relative error* | 0.32% | 0.39% | 0.23% | 0.24% | 0.19% |

*The mean error relative to the average concentration of the parameter.

These errors are very low compared to the typical prediction error of 0.8% relative against the values of these components as determined by known wet chemistry methods.

It will be appreciated by the skilled artisan that the application of the method according to the present invention permits greater standardisation of the outputs between different instruments 100 of the same type as well as the standardisation of outputs of the same instrument 100 as the pathlength through the cuvette 620 changes.

As will also be appreciated by the skilled artisan, instead of expressing the spectral information about the electromagnetic radiation in terms of a wavenumber, one may instead use a wavelength or a frequency without departing from the invention as claimed.

The invention claimed is:

1. A method of correcting for an amplitude change in an output of a spectrometric instrument due to variations in an optical path length through a sample holder, the method comprising:

exposing an unknown sample in the sample holder to electromagnetic radiation at a plurality of wavenumbers;

detecting, by the spectrometric instrument, electromagnetic absorption intensities in the unknown sample at the plurality of wavenumbers;

providing, to a computer device, associated with the spectrometric instrument the detected electromagnetic absorption intensities indexed against wavenumber as spectral data;

generating, by the computer device, absorbance values relative to a zero material sample from the spectral data;

applying, by the computer device, a mathematical transform ($I_{corr}$) to the generated absorbance values to correct for the amplitude change in the output of the spectrometric instrument;

wherein the method further includes calculating, in the computer device, the mathematical transform ($I_{corr}$) by determining a difference ($\Delta(SB_Z)'$) between a first derivative of a logarithmic transformation of spectral data ($SB_Z$) from the zero material sample at a first wavenumber range ($x_1$) ($\log_{10}(SB_Z(x_1))'$), and a first derivative of a logarithmic transformation of the spectral data ($SB_Z$) from the zero material sample at a second wavenumber range ($x_2$) ($\log_{10}(SB_Z(x_2))'$), and calculating, in the computer device, the mathematical transform ($I_{corr}$) as a function inversely dependent on the determined difference ($\Delta(SB_Z)'$).

2. The method according to claim 1, wherein calculating the mathematical transform ($I_{corr}$) includes correcting for humidity present in air in a light path between a radiation device and a detector of the spectrometric instrument by determining a humidity correction factor ($corr_{hum}$) as a slope/intercept on selected humidity regions of the spectral data ($SB_Z$) from the zero material sample; and calculating the mathematical transform ($I_{corr}$) as a function inversely dependent on a sum of the determined difference ($\Delta(SB_Z)'$) and the humidity correction factor ($corr_{hum}$).

3. The method according to claim 1, wherein the zero material sample comprises a nominally pure water sample.

4. The method according to claim 1, wherein the detected electromagnetic absorption intensities are detected by Fourier transform spectroscopy.

5. The method according to claim 1, wherein the spectral data ($SB_Z$) from the zero material sample comprises wavenumber standardized spectral data.

6. An apparatus, comprising:

a spectrometric instrument configured to perform Fourier transform spectroscopy on a sample in a sample holder; and an associated computing device configured to receive spectral data from the spectrometric instrument and to apply thereto a mathematical transform stored in a memory accessible to the associated computing device, which transform corrects the spectral data for amplitude change in electromagnetic absorption intensities detected by the spectrometric instrument;

wherein the associated computing device is programmed to operate to cause the apparatus to perform the method according to claim 1.

7. The method according to claim 2, wherein the mathematical transform ($I_{corr}$) is calculated as a reciprocal of an inverse intensity correction ($1/I_{corr}$) that is calculated according to equation (1), $$(1/I_{corr}) = c_1 \cdot \Delta(SB_Z)' + c_2 + (corr_{hum}) \quad (1)$$

wherein, in equation (1), $c_1$ is a first empirically-determined constant that is based solely on an absorption of water relative to air at a particular nominal optical path length $L_0$, $c_2$ is a second empirically-determined constant that is based on a contribution to a background due to dry air, and ($corr_{hum}$) is calculated according to equation (2), $$(corr_{hum}) = -\log_{10}\left[\frac{Peak_1}{Peak_2}\right]c_3 + c_4 \quad (2)$$

wherein, in equation (2), $Peak_1$ and $Peak_2$ are respective intensities of an adjacent valley and peak in a fringe pattern in an infrared region of the spectral data ($SB_Z$) from the zero material sample that is associated with a presence of humidity in the light path, $c_3$ is a third empirically-determined constant that is based on an influence of humidity on the mathematical transform ($I_{corr}$), and $c_4$ is a fourth empirically-determined constant that indicates an offset between the intensities at $Peak_1$ and $Peak_2$ when no humidity is present in the light path.

8. A computing device, comprising:

a memory storing a program of instructions; and a processor configured to execute the program of instructions to perform a method of correcting for an amplitude change in an output of a spectrometric instrument due to variations in an optical path length through a sample holder, the method including generating, by the computer device, absorbance values relative to a zero material sample from spectral data received from the spectrometric instrument, the spectral data indicating electromagnetic absorption intensities that are detected, by the spectrometric instrument, in an unknown sample in that is exposed to electromagnetic radiation in the sample holder at a plurality of wavenumbers, the spectral data indicating the electromagnetic absorption intensities indexed against wavenumber, and applying, by the computer device, a mathematical transform ($I_{corr}$) to the generated absorbance values to correct for the amplitude change in the output of the spectrometric instrument, wherein the method further includes calculating, in the computer device, the mathematical transform ($I_{corr}$) by determining a difference ($\Delta(SB_Z)'$) between a first derivative of a logarithmic transformation of spectral data ($SB_Z$) from the zero material sample at a first wavenumber range ($x_1$) ($\log_{10}(SB_Z(x_1))'$), and a first derivative of a logarithmic transformation of the spectral data ($SB_Z$) from the zero material sample at a second wavenumber range ($x_2$) ($\log_{10}(SB_Z(x_2))'$), and calculating, in the computer device, the mathematical transform ($I_{corr}$) as a function inversely dependent on the determined difference ($\Delta(SB_Z)'$).

9. The computing device according to claim 8, wherein calculating the mathematical transform ($I_{corr}$) includes Correcting for humidity present in air in a light path between a radiation device and a detector of the spectrometric instrument by determining a humidity correction factor ($corr_{hum}$) as a slope/intercept on selected humidity regions of the spectral data ($SB_Z$) from the zero material sample; and calculating the mathematical transform ($I_{corr}$) as a function inversely dependent on a sum of the determined difference ($\Delta(SB_Z)'$) and the humidity correction factor ($corr_{hum}$).

10. The computing device according to claim 8, wherein the zero material sample comprises a nominally pure water sample.

11. The computing device according to claim 8, wherein the electromagnetic absorption intensities are detected by Fourier transform spectroscopy.

12. The computing device according to claim 8, wherein the spectral data ($SB_Z$) from the zero material sample comprises wavenumber standardized spectral data.

13. The computing device according to claim 9, wherein the mathematical transform ($I_{corr}$) is calculated as a reciprocal of an inverse intensity correction ($1/I_{corr}$) that is calculated according to equation (1), $$(1/I_{corr}) = c_1 \Delta(SB_Z) + c_2 + (corr_{hum}) \qquad (1)$$

wherein, in equation (1), $c_1$ is a first empirically-determined constant that is based solely on an absorption of water relative to air at a particular nominal optical path length $L_0$, $c_2$ is a second empirically-determined constant that is based on a contribution to a background due to dry air, and ($corr_{hum}$) is calculated according to equation (2), $$(corr_{hum}) = -\log_{10}\left[\frac{Peak_1}{Peak_2}\right]c_3 + c_4 \qquad (2)$$

wherein, in equation (2), $Peak_1$ and $Peak_2$ are respective intensities of an adjacent valley and peak in a fringe pattern in an infrared region of the spectral data ($SB_Z$) from the zero material sample that is associated with a presence of humidity in the light path, $c_3$ is a third empirically-determined constant that is based on an influence of humidity on the mathematical transform ($I_{corr}$), and $c_4$ is a fourth empirically-determined constant that indicates an offset between the intensities at $Peak_1$ and $Peak_2$ when no humidity is present in the light path.

* * * * *